United States Patent [19]

Monnier

[11] Patent Number: 5,536,851
[45] Date of Patent: Jul. 16, 1996

[54] PREPARATION OF 2,3-DIHYDROFURANS

[75] Inventor: John R. Monnier, Kingsport, Tenn.

[73] Assignee: Eastman Chemical Company, Kingsport, Tenn.

[21] Appl. No.: 381,595

[22] Filed: Jan. 31, 1995

[51] Int. Cl.$^6$ .................................................. C07D 315/00
[52] U.S. Cl. ........................................... 549/507; 549/429
[58] Field of Search ..................................... 549/429, 507

[56]     References Cited

U.S. PATENT DOCUMENTS

| | | | |
|---|---|---|---|
| 3,651,092 | 3/1972 | Stapp et al. | 549/429 |
| 4,962,210 | 10/1990 | Falling et al. | 549/429 |
| 5,254,701 | 10/1993 | Falling et al. . | |

FOREIGN PATENT DOCUMENTS 674652   1/1968   Germany .
1248669   1/1968   Germany .

*Primary Examiner*—Nathan M. Nutter
*Assistant Examiner*—Richard Jones
*Attorney, Agent, or Firm*—J. Frederick Thomsen; Harry J. Gwinnell

[57]     ABSTRACT

Disclosed is a process for the preparation of 2,3-dihydrofurans from the corresponding isomeric 2,5-dihydrofurans wherein a feed mixture comprising a 2,5-dihydrofuran compound and an aldehyde selected from alkanals containing 2 to 5 carbon atoms and alkenals containing 3 or 4 carbon atoms, an epoxide selected from 1,2-epoxyalkanes containing 2 to 5 carbon atoms and 3,4-epoxy-1-butene, or a mixture of 2 or more of such aldehydes or epoxides and, optionally, carbon monoxide is contacted with a supported, palladium or platinum catalyst to effect the isomerization of 2,5-dihyrofurans to 2,3-dihydrofurans.

8 Claims, No Drawings

PREPARATION OF 2,3-DIHYDROFURANS

This invention pertains to an improved process for preparing 2,3-dihydrofurans from the corresponding isomeric 2,5-dihydrofurans. More specifically, this invention pertains to the catalytic isomerization of 2,5-dihyrofurans to 2,3-dihydrofurans by contacting in a heterogenous mode of operation a 2,5-dihydrofuran with a supported, palladium or platinum catalyst in the presence of certain epoxides and/or aldehydes and, optionally, carbon monoxide. The 2,3-dihydrofurans produced by the present process are useful as intermediates for the manufacture of precursors for polymers and pharmaceuticals. For example, 2,3-dihydrofuran is readily converted according to known processes into 1,4-butanediol, a precursor monomer used in the manufacture of polyurethanes and polyesters, and cyclopropanecarboxaldehyde, a compound which may be used in the synthesis of physiologically active compounds.

It is known (U.S. Pat. No. 2,556,325) that 2,5-dihydrofurans may be isomerized to 2,3-dihydrofurans in the presence of alkali metal alkoxides. German Patent 1,248,669 discloses the catalytic isomerization of 2,5-dihydrofuran to 2,3-dihydrofuran using certain metal catalysts such as palladium, platinum, cobalt, ruthenium and nickel. However, the selectivity of the process of German Patent 1,248,669 for converting 2,5-dihydrofurans to the desired 2,3-dihydrofuran is only in the 75–85% range.

Finally, U.S. Pat. No. 3,651,092 teaches the use of a supported nickel/arsenic catalyst in the presence of a combination of hydrogen and carbon monoxide. Again, however, the selectivity to the desired 2,3-dihydrofuran is relatively low. It should be noted that hydrogen is always utilized in this patent and that carbon monoxide, when used, is always combined with hydrogen. U.S. Pat. No. 5,254,701 discloses a homogeneous process for the production of a mixture of 2-hydroxytetrahydrofuran and 4-hydroxybutanal by the steps of (1) heating 2,5-dihydrofuran in the presence of a catalyst system comprising a tertiary phosphine and ruthenium or rhodium to convert the 2,5-dihydrofuran to 2,3-dihydrofuran and (2) contacting 2,3-dihydrofuran with water in the presence of an acidic catalyst to convert the 2,3-dihydrofuran to a mixture of 2-hydroxytetrahydrofuran and 4-hydroxybutanal.

The present invention provides a process for the preparation of a 2,3-dihydrofuran (2,3-DHF) compound which comprises contacting at an elevated temperature a 2,5-dihydrofuran (2,5-DHF) with a supported, palladium or platinum catalyst in the presence of a selectivity-increasing amount of an aldehyde selected from alkanals containing 2 to 5 carbon atoms and alkenals containing 3 or 4 carbon atoms, an epoxide selected from 1,2-epoxyalkanes containing 2 to 5 carbon atoms and 3,4-epoxy-1-butene, or a mixture of 2 or more of such aldehydes or epoxides. The selectivity of the novel isomerization process typically is in excess of 85 mole percent and, when operating under a preferred combination of process conditions and in the presence of carbon monoxide, selectivity typically exceeds 95 mole percent. As is known to those skilled in the art, conversion and selectivity commonly are interrelated in catalytic processes and an increase in one typically results in a decrease in the other. Nickel, rhodium and ruthenium have been found to be less effective than palladium and platinum as catalysts for the process.

The 2,5-DHF compounds constituting the reactants or feed materials in our novel process and the 2,3-DHF products may be mono- or bi-cyclic, unsubstituted or substituted compounds containing up to about 20 carbon atoms. Examples of the 2,5-DHF and 2,3-DHF compounds are those having the structural formulas:

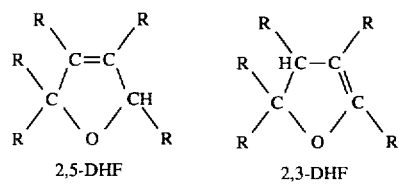

wherein each R is independently selected from hydrogen and $C_1$–$C_4$ alkyl groups or 2 R substituents collectively may represent an alkylene radical which forms a ring having about 5 to 8 carbon atoms. Each R preferably is hydrogen or methyl. The reactant and product compounds preferably contain up to a maximum of 7 carbon. Specific examples of the 2,5-dihydrofurans reactants include 2,5-dihydrofuran, 2,5-dimethyl-2,5-dihydrofuran, 2,2,5-trimethyl-2,5-dihydrofuran, 2-methyl-2,5-dihydrofuran, 2,2,3,4,5-pentamethyl-2,5-dihydrofuran and the like. Of the compounds which may be obtained in accordance with our invention, the most important is 2,3-dihydrofuran.

The present isomerization process may be carried out under a broad range of pressure and temperature conditions. Pressure is not an important feature of the process and thus pressures moderately above or below atmospheric are used. Pressures of 1–50 bars absolute, preferably 1–30 bars absolute, and most preferably 1–20 bars absolute may be used. It is apparent that vapor phase operation requires the use of pressures which, in combination with the process temperature, will cause the reactant and product to be present in the reactor as vapors. The isomerization may be carried out at temperatures in the range of about 30° to 200° C., preferably in the range of about 40° to 185° C., and most preferably in the range of about 50° to 175° C. Generally, the temperatures employed with platinum catalysts are higher than those used with palladium catalysts.

Examples of the epoxides and aldehydes which may be used the process to provide an increase in selectivity include those having the general formulas

wherein $R^1$ is hydrogen, $C_1$–$C_3$ alkyl or vinyl and $R^2$ is $C_1$–$C_4$ alkyl, vinyl or allyl. Specific examples of the epoxides and aldehydes include 3,4-epoxy-1-butene (EpB), ethylene oxide, propylene oxide, butylene oxide, crotonaldehyde, acetaldehyde, propionaldehyde, n-butyraldehyde, isobutyraldehyde, valeraldehydes, acrolein and vinyl acetaldehyde. These compounds may be added to the 2,5-DHF feedstream intentionally or be present in the feedstream as impurities, e.g., 1,3-butadiene may be selectively oxidized to EpB which in turn can be converted to 2,5-DHF, all according to known processes, to give 2,5-DHF which may contain trace or minor amounts of crotonaldehyde and/or EpB.

The amount of the above-described epoxides and/or aldehydes which may be used to exert a favorable effect on selectivity varies substantially depending upon such factors as the particular catalyst and reaction conditions, especially temperature, used and the mode of operation, e.g., gas or liquid phase. Generally, the amount of epoxide/aldehyde present in the feed to the isomerization process is in the range of about 5 to 20,000 parts per million by volume (ppmv), preferably 10 to 10,000 ppmv and, most preferably, 100 to 5000 ppmv based on the total volume of the gas fed to the reactor, i.e., the volume of the 2,5-DHF reactant and any diluent gas or liquid present.

When employed at the optimum concentrations, the above-described epoxides and/or aldehydes give high selectivity with essentially no decrease in the rate of 2,3-DHF formation and, thus, the space time yield (STY) of 2,3-DHF increases for the optimum co-feed amount of epoxide/aldehyde. A particularly advantageous feature of the novel process is that the effect of the epoxide and/or aldehyde is reversible. Thus, removal of the epoxide/aldehyde from the process restores the activity of the catalyst to that which existed before the epoxide/aldehyde was added. This phenomenon is referred to as reversible Langmuir adsorption, which simply means that the effect of the epoxide/aldehyde is reversible and is controlled by the level of epoxide/aldehyde employed in the process. This very desirable feature allows the catalyst performance to be modified as needed over a wide range of performance parameters by simply changing the amount of epoxide/aldehyde being added to the feedstream. Because catalyst activity generally decreases with increasing levels of epoxide/aldehyde, while selectivity to the desired 2,3-DHF product increases with increasing levels of epoxide/aldehyde, the desired combination of activity and selectivity to the 2,3-DHF compound can be selected by adjusting the amount of epoxide/aldehyde in the feed.

Carbon monoxide optionally may be used in combination with one or more of the above-described epoxides and aldehydes to enhance selectivity. For example, carbon monoxide may be added to a 2,5-DHF reactant which contains only a trace amount of such epoxide and/or aldehyde to achieve a desired combination of selectivity and conversion. It is apparent that the amount of the carbon monoxide which, in combination with one or more of the above-described epoxides and/or aldehydes, will enhance the selectivity of the catalytic process can vary substantially depending upon such factors as the amount of epoxide/aldehyde present in the 2,5-DHF reactant, the particular catalyst and reaction conditions, especially temperature, used and the mode of operation, e.g., gas or liquid phase. Generally, the amount of carbon monoxide which optionally may be added to the feed is in the range of about 5 to 5,000 ppmv based on the total volume of the gas fed to the reactor, i.e., the volume of the 2,5-DHF reactant and volumes of the above-described epoxides and/or aldehydes and any diluent gas or liquid present. Those skilled in the art will recognize that operation in the liquid phase may require carbon monoxide concentrations higher than those used in vapor phase operation. This is required to achieve adequate levels of carbon monoxide dissolved in the liquid. Thus, liquid phase operation requires carbon monoxide concentrations of about 5 to 5000 ppmv in the liquid fed to the reactor. In gas phase operation, the carbon monoxide concentration preferably is about 10 to 200 ppmv, most preferably about 20 to 100 ppmv. A typical carbon monoxide concentration in the feed in gas phase operation is about 25 ppmv. As in the case of the above-described epoxides/aldehydes, the effect of carbon monoxide also is reversible and thus, the removal of both epoxide/aldehyde and carbon monoxide from the process restores the activity of the catalyst to that which existed before the epoxide/aldehyde and carbon monoxide were added.

The performance characteristics of heterogeneous catalysts usually are modified by adding solid addenda to the surface of the active catalyst, which often is an imprecise approach and not easily controlled since it is largely irreversible. Thus, one is left with the particular performance characteristics of that catalyst composition. A "tunable" catalyst performance is very desirable when the feed composition changes, heat transfer conditions change or if selectivity demands change for a particular application.

The supported catalysts used in the present invention comprise palladium, platinum, or a mixture thereof, in the form of metals, deposited on a catalyst support material. The amount of the palladium and/or platinum metal component of the catalysts may be in the range of about 0.1 to 10 weight percent with amounts of about 0.2 to 5.0 weight percent being preferred. Supported catalysts comprising 0.5 to 3.0 weight percent palladium are particular preferred.

The support material component of the catalysts may be selected from the large number of nonacidic, conventional, porous, refractory catalyst carriers or support materials which are essentially inert in the presence of the reactant, product, diluent and carbon monoxide present in the processes in which the catalysts are employed. Such conventional materials may be of natural or synthetic origin and preferably are of a mesoporous or macroporous structure, i.e., support materials having a surface area below about 100 square meters per gram ($m^2/g$). These support materials typically have an apparent porosity of greater than 20%. Supports having a siliceous and/or aluminous composition are, in general, preferred.

Specific examples of suitable supports are the aluminum oxides (including the materials sold under the trade name "Alundum"), pumice, magnesia, zirconia, kieselguhr, fuller's earth, silicon carbide, porous agglomerates comprising silicon and/or silicon carbide, silica, selected clays, artificial and natural Zeolites and ceramics. Refractory supports particularly useful in the preparation of the catalysts useful in the process of our invention comprise siliceous and/or aluminous materials, and in the case of aluminous materials, particularly those containing alpha alumina. In the case of alpha alumina-containing supports, preference is given to those having a specific surface area as measured by the B.E.T. method of from about 0.03 to 10 $m^2/g$ and an apparent porosity as measured by conventional mercury or water absorption techniques of from about 25 to about 50% by volume. The B.E.T. method for determining specific surface area is described in detail in Brunauer, S., Emmett, P. H., and Teller, E., J. Am. Chem. Soc., 60, 309–16 (1938).

The following materials are specific examples of the catalyst supports which may be used.

I. Star-shaped silica support, typically having a surface area of 20–80 $m^2/g$, a total pore volume of 0.3 to 0.7 cc(Hg)/g, median pore diameter of 100–500 microns (μ), and a chemical composition composed substantially of $SiO_2$.

II. Norton SN-08228, 0.1875 inch pellets with a surface area of 0.26 $m^2/g$, a total pore volume of 0.23 cc (Hg)/gm, median pore diameter of 19μ, a packing density of 0.90 g/$cm^3$, and a chemical composition (weight percent) of: alumina—84.7, $SiO_2$—13.4, $Fe_2O_3$—0.21, $TiO_2$—0.47, CaO—0.21, MgO—0.12, $Na_2O$—0.15, $K_2O$—0.26.

III. Norton SA-5252, 0.1875 inch spheres with a surface area of 0.39 $m^2/g$, a total pore volume of 0.36 cc(Hg)/gm, median pore diameter of 5.4μ, a packing density of 0.94 g/$cm^3$ and a chemical composition (weight percent) as follows: $Al_2O_3$—93.1, $SiO_2$—5.6, $Fe_2O_3$—0.3, $TiO_2$—0.1, CaO—0.1, MgO—0.3, $Na_2O$—0.1, $K_2O$—0.1.

IV. Norton 5552 Alumina Rings—0.25 inch rings having a surface area of 0.43 $m^2/g$, a total pore volume of 0.37 cc (Hg)/gm, a median pore diameter of 7μ, a packing density of 0.80 g/$cm^3$, and a chemical composition (weight percent) of: $Al_2O_3$—93.1, $SiO_2$—5.6, $Fe_2O_3$—0.3, $TiO_2$—0.1, CaO—0.1, MgO—0.3, $Na_2O$—0.1, $K_2O$—0.1.

V. Norton SN-82501, 0.1875 inch spheres having a surface area of 0.13 m$^2$/g, a total pore volume of 0.37 cc(Hg)/gm, a median pore diameter of 32.5µ, a packing density of 0.88 g/cm$^3$, and a chemical composition (weight percent) of: Al$_2$O$_3$—85.0, SiO$_2$—12.0, and the remaining 3% as Fe$_2$O$_3$, TiO$_2$, CaO, MgO, Na$_2$O and K$_2$O.

Although not preferred, other support materials which may be used include zinc oxide, e.g., having a surface area of about 3–10 m$^2$/g and a particle size of about 75–250µ; titania, e.g., having a surface area of about 0.5 m$^2$/g and a particle size of about 40–75µ; calcium oxide; barium oxide, e.g., having a surface area of about 1 m$^2$/g and a particle size of 40–75µ; boron nitride; and silicon carbide.

A preferred class of support materials comprise extruded star-shaped silica supports which have relatively uniform pore diameters and are more fully characterized by having (1) B.E.T. specific surface areas of from about 20 m$^2$/g to about 80 m$^2$/g, preferably about 70 m$^2$/g, and (2) apparent porosities of from about 20% to about 70%, preferably from about 30% to about 60%.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid-solid contacting, catalyst durability, and the like make the use of defined shapes such as stars, spheres, pellets, extrudates, rings, saddles, and the like preferred.

The process of the invention may be carried out in the vapor phase by feeding a mixture of the 2,5-DHF reactant, one or more of the epoxides and/or aldehydes described herein and, optionally, carbon monoxide and/or an inert, gaseous diluent to a reactor containing one or more beds of one or more of the catalyst described above. The operation of the process without feeding an inert diluent to the reactor simplifies reactant/product separation downstream from the reactor. The use of a diluent as well as the amount thereof depends upon a plurality of factors including the particular design or configuration of the reactor since heat generated by the isomerization process must be removed from the reactor. Examples of diluents which may be used include helium, argon., krypton, neon, carbon dioxide, nitrogen and/or one or more C$_1$–C$_8$ alkanes. The diluent:2,5-DHF reactant volume ratio may be in the range of about 1:10 to 1:0.02 with volume ratios in the range of about 1:1 to 1:0.1 being more typical. Unlike the process described in U.S. Pat. No. 3,651,092 the process of this invention preferably is carried out in the substantial absence of hydrogen, e.g., hydrogen is not intentionally added to the 2,5-DHF reactant and/or optional diluent.

The gas hourly space velocity (GHSV) used in vapor phase operation of the process typically is between about 100 and 10,000, with GHSV's in the range of about 200 to 8000 being preferred and values of 300 to 5000 being most preferred. GHSV is the volume of gas (reactant plus any diluent used) fed to the reactor per hour divided by the volume of the catalyst present in the reactor. The degree of conversion of the 2,5-DHF reactant fed to the desired 2,3-DHF product is inversely proportional to the GHSV employed, provided other process parameters are the same. Thus, the degree of conversion desired determines the GHSV which is used.

The process also may be operated in the liquid phase. One mode of liquid operation comprises feeding a two-phase, liquid mixture comprising liquid 2,5-DHF reactant, epoxide/aldehyde and, optionally, gaseous carbon monoxide and an inert diluent which is liquid under the process conditions to a reactor containing one or more beds of one or more catalysts. The liquid mixture flows, e.g., in an upward direction, over the catalyst in a mode of operation referred to as flooded bed operation. A suitable diluent in such liquid phase operation is the 2,3-DHF product of the process. Typical 2,5-DHF:2,3-DHF weight ratios which may be fed to liquid phase operation of the present process are in the range of about 1:10 to 1:0.1.

In another mode of liquid operation, a mixture comprising the 2,5-DHF reactant, gaseous carbon monoxide and, optionally, an inert, gaseous diluent is fed to an inert, liquid diluent or reaction medium, e.g. a hydrocarbon paraffin such as mineral oil, in which the catalyst is suspended. The 2,3-DHF product is removed from the liquid reaction medium as a vapor.

Our novel process is further illustrated by the following examples. The procedures of the examples utilized a single pass, vapor phase reactor constructed of Pyrex glass tubing. The catalyst charge was held in position by a Pyrex glass frit. The geometry of the reactor (10 mm inside diameter) and catalyst particles (0.4 to 0.8 mm diameter) were chosen to maintain and measure true kinetic and catalytic aspects of the reaction. A thermocouple (Chromel/Alumel alloy) sheathed in stainless steel was embedded within the catalyst bed to measure the true reaction temperature.

The reactor was loaded with 1.25 a supported catalyst consisting of 1.0 weight percent palladium on silica extrudates. The catalyst was pretreated in situ with a gas mixture consisting of 20 volume percent hydrogen and 80 volume percent helium at 225° C. for 2.0 hours. A vapor of 2,5-DHF and helium was added to the feed stream by sweeping helium through a liquid reservoir of 2,5-DHF maintained at a predetermined temperature, usually 20° C., such that the 2,5-DHF:helium volume ratio varied between 1:20 to 1:4. EpB or crotonaldehyde also was added from individual vapor-liquid equilibrium saturators maintained at the proper temperatures and flow rates to give the desired concentration of EpB/crotonaldehyde in the feedstreams. Carbon monoxide was supplied to the feedstreams using electronic mass flow controllers connected to a gas supply containing 1000 ppmv of carbon monoxide in helium. The actual levels of carbon monoxide in the feedstream were determined by controlling the gas flow rates of the carbon monoxide/helium mixture in the total flow of 2,5-DHF, the above-described epoxides/aldehydes, helium and carbon monoxide. In these cases, typical 2,5-DHF concentrations were similar to those employed when no carbon monoxide was added to the feedstream. The 2,5-DHF used in the examples was of very high purity and contained no other detectable organic components. All gas flows were delivered using mass flow controllers.

Gas chromatography analyses were made using in-line gas sampling valves which permitted the analysis of the gas stream both above and below the catalyst bed. All reactor feed and effluent lines were heated at 100° C. to prevent condensation of feed and/or effluent materials. The levels of conversion were determined by comparing the composition of the gas stream above the catalyst bed with that below the catalyst bed. The gas chromatographic separations were made using a 10 foot (3.05 meters)-long Pyrex glass column (2 mm internal diameter) packed with Carbowax polyalkylene glycol 20M (20%) supported on Chromosorb W diatomite aggregate, acid washed. The non-selective co-products formed in the process consisted primarily of furan and tetrahydrofuran, in approximately equal amounts.

EXAMPLES 1–4 AND COMPARATIVE EXAMPLES C-1 AND C-2

2,5-DHF was converted to 2,3-DHF according to the above-described vapor phase procedure using a reaction temperature of 90° C. and a feed gas consisting of 2,5-DHF and helium and differing amounts of EpB and carbon monoxide, including no EpB and/or carbon monoxide in the comparative examples. The 2,5-DHF:total helium volume ratio of the feed gas was 1:15. 2,5-DHF was fed to the reactor at a rate of 0.043 g per minute. The experiments constituting Examples 1–4 and Comparative Examples C-1 and C-2 were carried out for a sufficient length of time to attain steady-state conditions.

The results obtained in these examples are set forth in Table I wherein the values for "EpB" and "CO" are ppmv concentration of 3,4-epoxy-1-butene and carbon monoxide, respectively, in the feed gas, "2,5-DHF Conv" is the mole percent conversion of 2,5-DHF defined as:

$$\frac{\text{Moles 2,5-DHF converted to products}}{\text{Moles 2,5-DHF fed}} \times 100$$

and "2,3-DHF Select" is the mole percent selectivity to 2,3-DHF defined as:

$$\frac{\text{Moles 2,5-DHF converted to 2,3-DHF}}{\text{Moles 2,5-DHF converted to total products}} \times 100$$

TABLE I

| Example | EpB | CO | 2,5-DHF Conv | 2,3-DHF Select |
|---------|------|-----|------|------|
| C-1 | 0 | 25 | 98.0 | 91.7 |
| 1 | 220 | 25 | 76.2 | 96.8 |
| 2 | 630 | 25 | 59.4 | 97.9 |
| 3 | 1400 | 25 | 46.5 | 97.5 |
| C-2 | 0 | 0 | 100.0 | 79.0 |
| 4 | 800 | 0 | 60.0 | 96.8 |

Table I shows the effect of an epoxide such as 3,4-epoxy-1-butene (EpB) at various levels, with and without carbon monoxide, on the conversion of 2,5-DHF 2,3-DHF in the presence of a palladium catalyst. Selectivity levels of 2,3-dihydrofuran at about 97–98% are achieved with or without carbon monoxide being present. A lower selectivity results when both EpB and carbon monoxide are absent whereas EpB in combination with carbon monoxide gives an improvement in selectivity when compared to that obtained with carbon monoxide alone. Because EpB functions in the same reversible manner as carbon monoxide, the carbon monoxide can be removed from the feedstream when sufficient EpB is present.

EXAMPLES 5–10 AND COMPARATIVE EXAMPLES C-3 AND C-4

The procedure used in the preceding examples were used in Examples 5–10 and Comparative Examples C-3 and C-4 except that differing amounts of crotonaldehyde, rather than EpB, were used. A fresh catalyst charge (1.25 g) activated in the manner described above was used in Examples 5–10 and Comparative Examples C-3 and C-4. The results obtained in these examples are set forth in Table II wherein "Croton" is the ppmv concentration of crotonaldehyde in the feed gas and "CO", "2 5-DHF Conv" and "2 3-DHF Select" have the meanings given above.

TABLE II

| Example | Croton | CO | 2,5-DHF Conv | 2,3-DHF Select |
|---------|--------|-----|------|------|
| C-3 | 0 | 0 | 100.0 | 31.6 |
| 5 | 620 | 0 | 68.7 | 95.6 |
| 6 | 1380 | 0 | 55.5 | 96.0 |
| 7 | 1970 | 0 | 49.5 | 96.2 |
| C-4 | 0 | 55 | 88.9 | 93.3 |
| 8 | 530 | 55 | 68.4 | 94.9 |
| 9 | 1040 | 55 | 58.1 | 95.7 |
| 10 | 2070 | 55 | 44.2 | 95.9 |

Table II shows the effect of various levels of crotonaldehyde, with or without carbon monoxide present, on the conversion of 2,5-DHF to 2,3-DHF using a palladium catalyst freshly pretreated and activated in a mixture of hydrogen and helium. Comparative Example C-3 shows that very low selectivity to 2,3-dihydrofuran occurs with no crotonaldehyde or carbon monoxide present. Comparative Example C-4 demonstrates that the presence of carbon monoxide alone gives an improvement in selectivity. However, an even greater improvement is obtained when carbon monoxide is combined with the crotonaldehyde (Examples 8–10) or is replaced altogether with a somewhat higher level of crotonaldehyde (Examples 5–7). The data show that carbon monoxide and crotonaldehyde have similar effects on catalyst performance. Thus, the actual level of carbon monoxide used as a feed additive can be balanced with the amount of crotonaldehyde present as a feed impurity or additive to achieve the optimum desired balance selectivity and conversion to 2,3-dihydrofuran.

The invention has been described in detail with particular reference to preferred embodiments thereof, but it will be understood that variations and modifications can be effected within the spirit and scope of the invention.

I claim:

1. Process for the preparation of a 2,3-dihydrofuran compound which comprises contacting at an elevated temperature a feed mixture of a 2,5-dihydrofuran compound and a selectivity-increasing amount of an aldehyde selected from alkanals containing 2 to 5 carbon atoms and alkenals containing 3 or 4 carbon atoms, an epoxide selected from 1,2-epoxyalkanes containing 2 to 5 carbon atoms and 3,4-epoxy-1-butene, or a mixture of 2 or more of such aldehydes or epoxides with a supported, palladium or platinum catalyst and in the substantial absence of hydrogen.

2. Process according to claim 1 wherein the process is carried out at a temperature of about 30° to 200° C., the feed mixture contains about 10 to 10,000 parts per million by volume of the epoxide, aldehyde or mixture thereof and the 2,5-dihydrofuran and 2,3-dihydrofuran compounds each contains up to 7 carbon atoms.

3. Process according to claim 1 wherein the process is carried out at a temperature of about 40° to 185° C., the feed mixture contains about 100 to 5000 parts per million by volume 3,4-epoxy-1-butene or crotonaldehyde and the 2,5-dihydrofuran and 2,3-dihydrofuran compounds each contains up to 7 carbon atoms and have the formulas:

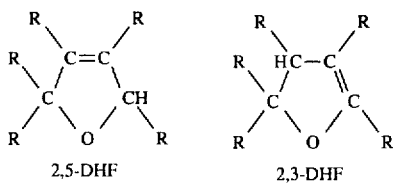

2,5-DHF    2,3-DHF wherein each R is independently selected from hydrogen and methyl.

4. Process according to claim 3 wherein the feed mixture also contains about 10 to 200 parts per million by volume carbon monoxide.

5. Process for the preparation of 2,3-dihydrofuran which comprises contacting a feed gas comprising 2,5-dihydrofuran, an inert diluent, and about 10 to 10,000 parts per million by volume 3,4-epoxy-1-butene or crotonaldehyde with a supported, palladium or platinum catalyst at a temperature of about 30° to 200° C. and in the substantial absence of hydrogen.

6. Process according to claim 5 for the preparation of 2,3-dihydrofuran which comprises contacting a feed gas comprising 2,5-dihydrofuran, an inert diluent, about 100 to 5000 parts per million by volume 3,4-epoxy-1-butene or crotonaldehyde and about 10 to 200 parts per million by volume carbon monoxide with a supported, palladium or platinum catalyst at a temperature of about 30° to 200° C.

7. Process according to claim 6 wherein the catalyst comprises about 0.2 to 5.0 weight percent palladium, platinum or a mixture thereof on a catalyst support material.

8. Process for the preparation of 2,3-dihydrofuran which comprises contacting a feed gas comprising 2,5-dihydrofuran, an inert diluent, about 100 to 5000 parts per million by volume 3,4-epoxy-1-butene or crotonaldehyde and about 20 to 200 parts per million by volume carbon monoxide with a supported palladium catalyst comprising about 0.5 to 3.0 weight percent palladium on a catalyst support material at a temperature of about 50° to 175° C. and in the substantial absence of hydrogen.

* * * * *